| (12) | United States Patent | (10) Patent No.: | US 10,994,110 B2 |
|---|---|---|---|
| | Ducharme | (45) Date of Patent: | May 4, 2021 |

(54) APPARATUS AND METHODS FOR DELIVERING THERAPEUTIC AGENTS

(71) Applicant: COOK MEDICAL TECHNOLOGIES LLC, Bloomington, IN (US)

(72) Inventor: Richard W. Ducharme, Pleasant Gap, PA (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 534 days.

(21) Appl. No.: 15/804,331

(22) Filed: Nov. 6, 2017

(65) Prior Publication Data

US 2018/0056052 A1 Mar. 1, 2018

Related U.S. Application Data

(62) Division of application No. 12/435,574, filed on May 5, 2009, now Pat. No. 9,839,772.

(Continued)

(51) Int. Cl.
*A61M 5/14* (2006.01)
*A61M 39/22* (2006.01)
(Continued)

(52) U.S. Cl.
CPC ............. *A61M 37/00* (2013.01); *A61B 1/018* (2013.01); *A61M 5/1409* (2013.01);
(Continued)

(58) Field of Classification Search
CPC ............ A61M 5/1409; A61M 5/15881; A61M 37/00; A61B 1/018
See application file for complete search history.

(56) References Cited

U.S. PATENT DOCUMENTS

| 39,678 A | 8/1863 | Russell |
|---|---|---|
| 170,182 A | 11/1875 | Molesworth |

(Continued)

FOREIGN PATENT DOCUMENTS

| CH | 15244 A | 9/1897 |
|---|---|---|
| CH | 257250 A | 3/1949 |

(Continued)

OTHER PUBLICATIONS

Office Action for Japanese Patent Application No. 2011-508588 dated Mar. 25, 2014, 6 pages including English translation.

(Continued)

*Primary Examiner* — Nathan R Price
*Assistant Examiner* — Weng Lee
(74) *Attorney, Agent, or Firm* — Brinks Gilson & Lione

(57) ABSTRACT

The present embodiments provide apparatus and methods suitable for delivering a therapeutic agent to a target site. The apparatus generally comprises at least one container for holding a therapeutic agent, and a pressure source for facilitating delivery of the therapeutic agent. In one embodiment, the pressure source may be placed in selective fluid communication with a proximal region of the container and fluid from the pressure source may flow through at least a portion of the container to urge the therapeutic agent through container towards the target site. In an alternative embodiment, the container and the pressure source may be coupled to first and second inlet ports of a connecting member, respectively, such that the therapeutic agent flows through an outlet port of the connecting member and towards the target site.

13 Claims, 6 Drawing Sheets

Related U.S. Application Data

(60) Provisional application No. 61/050,906, filed on May 6, 2008.

(51) Int. Cl.

| | | |
|---|---|---|
| *A61M 37/00* | (2006.01) | |
| *A61B 1/018* | (2006.01) | |
| *A61M 5/168* | (2006.01) | |
| *A61M 39/24* | (2006.01) | |

(52) U.S. Cl.
CPC ....... *A61M 5/16881* (2013.01); *A61M 39/223* (2013.01); *A61M 39/24* (2013.01)

(56) References Cited

U.S. PATENT DOCUMENTS

| | | |
|---|---|---|
| 280,202 A | 6/1883 | Mattson |
| 442,785 A | 12/1890 | Schoettl |
| 460,458 A | 9/1891 | Bates |
| 471,865 A | 3/1892 | Howard |
| 533,489 A | 2/1895 | Ogram |
| 566,411 A | 8/1896 | Schoene |
| 576,437 A | 2/1897 | Elliot |
| 693,587 A | 2/1902 | Campbell |
| 775,985 A | 11/1904 | McKain |
| 881,238 A | 3/1908 | Hasbrouck |
| 904,149 A | 11/1908 | Rachmann |
| 938,648 A | 11/1909 | DeVilbiss |
| 1,022,601 A | 4/1912 | Rumberg et al. |
| 1,114,114 A | 10/1914 | Cochenour |
| 1,145,520 A | 7/1915 | Smith |
| 1,261,503 A | 4/1918 | Figgis |
| 1,357,452 A | 11/1920 | Hall |
| 1,466,119 A | 8/1923 | Claflin |
| 1,521,396 A | 12/1924 | Scott |
| 1,685,280 A | 9/1928 | Findley |
| 1,934,793 A | 11/1933 | Crain et al. |
| 2,004,402 A | 6/1935 | Conklin |
| 2,151,418 A | 3/1939 | Bolte |
| 2,223,611 A | 12/1940 | Gross |
| 2,307,986 A | 1/1943 | Bolte et al. |
| 2,390,313 A | 12/1945 | Macgill |
| 2,507,702 A | 5/1950 | Fields |
| 2,519,555 A | 8/1950 | Fields |
| 2,609,155 A | 9/1952 | Fosnaugh |
| 2,632,444 A | 3/1953 | Kas |
| 2,805,013 A | 9/1957 | Cordis |
| 2,934,314 A | 4/1960 | Chambers et al. |
| 2,956,579 A | 10/1960 | Moore et al. |
| 3,016,895 A | 1/1962 | Sein et al. |
| 3,050,261 A | 8/1962 | Littlefield |
| 3,506,008 A | 4/1970 | Huck |
| 3,540,444 A | 11/1970 | Moreland |
| 3,572,335 A | 3/1971 | Robinson |
| 3,589,363 A | 6/1971 | Banko et al. |
| 3,599,866 A | 8/1971 | Bolton |
| 3,632,046 A | 1/1972 | Hengesbach |
| 3,647,143 A | 3/1972 | Gauthier et al. |
| 3,649,299 A | 3/1972 | Sholl |
| 3,667,465 A | 6/1972 | Voss |
| 3,710,400 A | 1/1973 | Sparks |
| 3,742,955 A | 7/1973 | Battista et al. |
| 3,744,493 A | 7/1973 | Booher et al. |
| 3,762,410 A | 10/1973 | Bindel |
| 3,788,315 A | 1/1974 | Laurens |
| 3,815,595 A | 6/1974 | Bar |
| 3,900,022 A | 8/1975 | Widran |
| 3,916,896 A | 11/1975 | Ballard |
| 4,009,637 A | 3/1977 | Bittner |
| 4,017,007 A | 4/1977 | Riccio |
| 4,040,420 A | 8/1977 | Speer |
| 4,174,811 A | 11/1979 | Binder et al. |
| 4,184,258 A | 1/1980 | Barrington et al. |
| 4,204,539 A | 5/1980 | Van Brugge |
| 4,204,645 A | 5/1980 | Hopp |
| 4,210,140 A | 7/1980 | James et al. |
| 4,359,049 A | 11/1982 | Redl et al. |
| 4,423,727 A | 1/1984 | Widran et al. |
| 4,427,650 A | 1/1984 | Stroetmann |
| 4,516,442 A | 5/1985 | Davis |
| 4,534,345 A | 8/1985 | Wetterlin |
| 4,539,716 A | 9/1985 | Bell |
| 4,578,067 A | 3/1986 | Cruz, Jr. |
| 4,606,501 A | 8/1986 | Bate et al. |
| 4,620,847 A | 11/1986 | Shishov et al. |
| 4,631,055 A | 12/1986 | Redl et al. |
| 4,637,816 A | 1/1987 | Mann |
| H257 H | 4/1987 | Barditch et al. |
| 4,655,211 A | 4/1987 | Sakamoto et al. |
| 4,735,616 A | 4/1988 | Eibl et al. |
| 4,738,658 A | 4/1988 | Magro et al. |
| 4,738,740 A | 4/1988 | Pinchuk |
| 4,752,466 A | 6/1988 | Saferstein et al. |
| 4,790,819 A | 12/1988 | Li et al. |
| 4,798,606 A | 1/1989 | Pinchuk |
| 4,803,977 A | 2/1989 | Kremer, Jr. |
| 4,846,405 A | 7/1989 | Zimmermann |
| D303,139 S | 8/1989 | Morga |
| 4,872,450 A | 10/1989 | Austad |
| 4,874,368 A | 10/1989 | Miller et al. |
| 4,890,612 A | 1/1990 | Kensey |
| 4,900,303 A | 2/1990 | Lemelson |
| 4,902,278 A | 2/1990 | Maget et al. |
| 4,902,281 A | 2/1990 | Avoy |
| 4,927,410 A | 5/1990 | Kovacs |
| 4,929,246 A | 5/1990 | Sinofsky |
| 4,941,874 A | 7/1990 | Sandow et al. |
| 4,941,880 A | 7/1990 | Burns |
| 4,945,050 A | 7/1990 | Sandford et al. |
| 4,946,870 A | 8/1990 | Partain, III et al. |
| 4,950,234 A | 8/1990 | Fujioka et al. |
| 4,969,874 A | 11/1990 | Michel et al. |
| 4,978,336 A | 12/1990 | Capozzi et al. |
| 4,994,028 A | 2/1991 | Leonard et al. |
| 5,015,580 A | 5/1991 | Christou et al. |
| 5,021,059 A | 6/1991 | Kensey et al. |
| 5,053,000 A | 10/1991 | Booth et al. |
| 5,059,187 A | 10/1991 | Sperry et al. |
| 5,061,180 A | 10/1991 | Wiele |
| 5,063,025 A | 11/1991 | Ito |
| 5,064,413 A | 11/1991 | McKinnon et al. |
| 5,106,370 A | 4/1992 | Stewart |
| 5,116,315 A | 5/1992 | Capozzi et al. |
| 5,120,657 A | 6/1992 | McCabe et al. |
| 5,129,825 A | 7/1992 | Discko, Jr. |
| 5,129,882 A | 7/1992 | Weldon et al. |
| 5,133,701 A | 7/1992 | Han |
| 5,141,515 A | 8/1992 | Eberbach |
| 5,147,292 A | 9/1992 | Kullas et al. |
| 5,149,655 A | 9/1992 | McCabe et al. |
| 5,165,604 A | 11/1992 | Copp, Jr. |
| 5,176,642 A | 1/1993 | Clement |
| 5,179,022 A | 1/1993 | Sanford et al. |
| D333,000 S | 2/1993 | Good et al. |
| 5,204,253 A | 4/1993 | Sanford et al. |
| 5,219,328 A | 6/1993 | Morse et al. |
| 5,226,567 A | 7/1993 | Sansalone |
| 5,226,877 A | 7/1993 | Epstein |
| 5,273,531 A | 12/1993 | Knoepfler |
| 5,292,309 A | 3/1994 | Van Tassel et al. |
| 5,310,407 A | 5/1994 | Casale |
| 5,312,333 A | 5/1994 | Churinetz et al. |
| 5,328,459 A | 7/1994 | Laghi |
| 5,337,740 A | 8/1994 | Armstrong et al. |
| 5,391,183 A | 2/1995 | Janzen et al. |
| 5,392,992 A | 2/1995 | Farnsteiner et al. |
| 5,395,326 A | 3/1995 | Haber et al. |
| 5,405,607 A | 4/1995 | Epstein |
| 5,415,631 A | 5/1995 | Churinetz et al. |
| 5,429,278 A | 7/1995 | Sansalore |
| 5,445,612 A | 8/1995 | Terakura et al. |
| 5,447,499 A | 9/1995 | Allaire et al. |
| 5,469,994 A | 11/1995 | Reh et al. |
| 5,470,311 A | 11/1995 | Setterstrom |

(56) References Cited

U.S. PATENT DOCUMENTS

| | | |
|---|---|---|
| 5,484,403 A | 1/1996 | Yaokum et al. |
| 5,503,623 A | 4/1996 | Tilton, Jr. |
| 5,513,630 A | 5/1996 | Century |
| 5,520,658 A | 5/1996 | Holm |
| 5,538,162 A | 7/1996 | Reh et al. |
| 5,553,741 A | 9/1996 | Sancoff et al. |
| 5,558,646 A | 9/1996 | Roche |
| 5,582,596 A | 12/1996 | Fukunaga et al. |
| 5,584,807 A | 12/1996 | McCabe |
| 5,584,815 A | 12/1996 | Pawelka et al. |
| 5,594,987 A | 1/1997 | Century |
| 5,601,603 A | 2/1997 | Illi |
| 5,605,541 A | 2/1997 | Holm |
| 5,612,050 A | 3/1997 | Rowe et al. |
| 5,665,067 A | 9/1997 | Linder et al. |
| 5,697,947 A | 12/1997 | Wolf et al. |
| 5,707,402 A | 1/1998 | Heim |
| 5,749,968 A | 5/1998 | Melanson et al. |
| 5,759,171 A | 6/1998 | Coelho |
| 5,788,625 A | 8/1998 | Plouhar et al. |
| 5,865,796 A | 2/1999 | McCabe |
| 5,873,530 A | 2/1999 | Chizinsky |
| 5,902,228 A | 5/1999 | Schulsinger et al. |
| 5,919,184 A | 7/1999 | Tilton, Jr. |
| 5,951,531 A | 9/1999 | Ferdman et al. |
| 6,007,515 A | 12/1999 | Epstein et al. |
| 6,013,050 A | 1/2000 | Bellhouse et al. |
| 6,021,776 A * | 2/2000 | Allred .............. A61M 11/02 128/200.14 |
| 6,027,471 A | 2/2000 | Fallon et al. |
| 6,059,749 A | 5/2000 | Marx |
| 6,077,217 A | 6/2000 | Love et al. |
| 6,117,150 A | 9/2000 | Pingleton et al. |
| 6,123,070 A | 9/2000 | Bruna et al. |
| 6,165,201 A | 12/2000 | Sawhney et al. |
| 6,368,300 B1 | 4/2002 | Fallon et al. |
| 6,394,975 B1 | 5/2002 | Epstein |
| 6,454,786 B1 | 9/2002 | Holm et al. |
| 6,461,325 B1 | 10/2002 | Delmotte et al. |
| 6,461,361 B1 | 10/2002 | Epstein |
| 6,478,754 B1 | 11/2002 | Babeav |
| 6,537,246 B1 | 3/2003 | Unger et al. |
| 6,610,026 B2 | 8/2003 | Cragg et al. |
| 6,616,652 B1 | 9/2003 | Harper |
| 6,641,800 B1 | 11/2003 | Mistry et al. |
| 6,689,108 B2 | 2/2004 | Lavi et al. |
| 6,716,190 B1 | 4/2004 | Glines et al. |
| 6,723,067 B2 | 4/2004 | Nielson |
| 6,811,550 B2 | 11/2004 | Holland et al. |
| 6,843,388 B1 | 1/2005 | Hollars |
| 6,863,660 B2 | 3/2005 | Marx |
| 6,939,324 B2 | 9/2005 | Gonnelli et al. |
| 7,101,862 B2 | 9/2006 | Chochrum et al. |
| 7,156,880 B2 | 1/2007 | Evans et al. |
| 7,291,133 B1 | 11/2007 | Kindler et al. |
| 7,334,598 B1 | 2/2008 | Hollars |
| 7,534,449 B2 | 5/2009 | Saltzman et al. |
| 7,544,177 B2 | 6/2009 | Gertner |
| 7,632,245 B1 | 12/2009 | Cowan et al. |
| 7,673,783 B2 | 3/2010 | Morgan et al. |
| 7,691,244 B2 | 4/2010 | Levitan et al. |
| 7,744,526 B2 | 6/2010 | McAllister et al. |
| 7,776,822 B2 | 8/2010 | Terman |
| 7,824,373 B2 | 11/2010 | Kim |
| 7,857,167 B1 | 12/2010 | Hollars |
| 2002/0169416 A1 | 11/2002 | Gonnelli |
| 2003/0023202 A1 | 1/2003 | Nielson |
| 2003/0108511 A1 | 6/2003 | Sawhney |
| 2003/0170250 A1 | 9/2003 | Ezrin et al. |
| 2003/0181917 A1* | 9/2003 | Gertner .............. A61M 15/0066 606/82 |
| 2003/0216695 A1 | 11/2003 | Yang |
| 2004/0073863 A1 | 4/2004 | Moulsley |
| 2005/0070848 A1 | 3/2005 | Kim et al. |
| 2006/0002852 A1 | 1/2006 | Saltzman et al. |
| 2006/0052295 A1 | 3/2006 | Terman |
| 2006/0286664 A1 | 12/2006 | Mcallister et al. |
| 2007/0240989 A1 | 10/2007 | Levitan et al. |
| 2007/0241119 A1 | 10/2007 | Durkin et al. |
| 2008/0027272 A1 | 1/2008 | Kadykowski |
| 2009/0007904 A1* | 1/2009 | Schuster .............. A61K 9/0073 128/200.23 |
| 2009/0234374 A1 | 9/2009 | Gabel et al. |
| 2009/0234380 A1 | 9/2009 | Gabel et al. |
| 2009/0248056 A1 | 10/2009 | Gabel et al. |
| 2010/0137796 A1 | 6/2010 | Perry et al. |

FOREIGN PATENT DOCUMENTS

| | | |
|---|---|---|
| DE | 3024749 A1 | 2/1982 |
| DE | 3108918 A1 | 9/1982 |
| DE | 3613762 A1 | 11/1987 |
| EP | 308269 A1 | 3/1989 |
| EP | 0 692 273 | 1/1996 |
| EP | 0738498 A1 | 10/1996 |
| GB | 10563 A | 12/1896 |
| GB | 1254534 A | 11/1971 |
| JP | 4022109 B | 4/1992 |
| JP | 5-192404 | 8/1993 |
| JP | 10-508790 | 9/1998 |
| JP | 2001-520918 | 11/2001 |
| JP | 2002-028224 | 1/2002 |
| JP | 2004-521677 | 7/2004 |
| SU | 978999 | 12/1982 |
| WO | WO 08/23545 | 10/1982 |
| WO | WO 1985/02346 | 6/1985 |
| WO | WO 1992/20312 | 11/1992 |
| WO | WO 1994/28798 | 12/1994 |
| WO | WO 96/009085 | 3/1996 |
| WO | WO 1996/025190 | 8/1996 |
| WO | WO 96/37245 | 11/1996 |
| WO | WO 96/40327 | 12/1996 |
| WO | WO 1997/20585 | 6/1997 |
| WO | WO 99/21599 | 5/1999 |
| WO | WO 02/055139 | 7/2002 |
| WO | WO 2002/053014 | 7/2002 |
| WO | WO 2004/073863 | 9/2004 |
| WO | WO 2005/100980 | 10/2005 |
| WO | WO 06/090149 | 8/2006 |
| WO | WO 2008/008845 | 1/2008 |

OTHER PUBLICATIONS

Office Action dated Jun. 12, 2013 for Japanese Patent Application No. 2011508588, 6 pages including English translation.
Response to Office Action dated Oct. 10, 2013 for Japanese Patent Application No. 2011-508588, 3 pages.
Response dated Mar. 14, 2012 for European Patent Application No. 09743424.5, 10 pgs.
Communication from European Patent Office dated Sep. 5, 2012 for European Patent Application No. 09743424.5, 6 pgs.
Response dated Feb. 22, 2013 for European Patent Application No. 09743424.5, 4 pgs.
Examination Report from European Patent Office dated Nov. 28, 2013 for European Patent Application No. 09743424.5, 6 pgs.
Examiner's Report dated Aug. 17, 2012 for Canadian Patent Application No. 2723183, 2 pgs.
Response to Examiner's Report dated Feb. 11, 2013 for Canadian Patent Application No. 2723183, 5 pgs.
Notice of Allowance dated Jul. 31, 2013 for Canadian Patent Application No. 2723183, 1 pg.
Examination Report No. 1 dated Sep. 27, 2012 for Australian Patent Application No. 2009244462, 4 pgs.
Response to Examination Report No. 1 dated Feb. 19, 2013 for Australian Patent Application No. 2009244462, 6 pgs.
Notice of Acceptance dated Apr. 2, 2013 for Australian Patent Application No. 2009244462, 3 pgs.
Certificate of Grant dated Jul. 25, 2013 for Australian Patent Application No. 2009244462, 1 pg.
Restriction Requirement for U.S. Appl. No. 12/633,027 dated May 25, 2012, 7 pgs.

(56) References Cited

OTHER PUBLICATIONS

Response to Restriction Requirement for U.S. Appl. No. 12/633,027 filed Jul. 2, 2012, 7 pgs.
International Preliminary Report on Patentability for PCT/US2009/042781, dated Nov. 18, 2010, 11 pgs.
Alto Shooter Catalog, Kaigen, English and Japanese, Jun. 1994, 8 pgs.
Decker, "An Efficient Method for the Application of Avitene Hemostatic Agent", Surgery, Gynecology & Obstetrics, 1981, vol. 172, No. 6, 2 pgs.
Endo-Avitene brochure, Med Chem Products, Inc. date unkown, 4 pgs.
Fagelman et al. "A Simple Method for Application of Microfibrilar Colagen", Surgery, Gynecology & Obstetrics, Jun. 1980, vol. 150, No. 6, 3 pgs.
Hoshino et al., "Trans-endoscopic Drug Propulsion Therapy", Diagnostic Endoscopy, 1993, vol. 5, 6 pgs.
Surgical Armamentarium, Copyright 1973 V. Mueller, 3 pgs.
Office Action dated Apr. 14, 2011 for U.S. Appl. No. 12/787,796, 9 pgs.
Response to Office Action filed Jul. 14, 2011 for U.S. Appl. No. 12/787,796, 11 pgs.
Notice of Allowance dated Oct. 18, 2011 for U.S. Appl. No. 12/787,796, 10 pgs.
PCT International Search Report and Written Opinion for PCT/2009/067076, 23 pgs.
International Search Report and Written Opinion for PCT/US2010/036381, dated Aug. 20, 2010, 16 pgs.
International Search Report completed Sep. 22, 2009 for PCT/US2009/042781, 7 pgs.
Hoshino, "Transendoscopic Projectile Drug Delivery", Gastroenterologia Japonica, vol. 25, No. 5, Jun. 15, 1990, 1 page.
Park et al., "A randomized comparison of a new flexible bipolar hemostasis forceps designed principally for NOTES versus a conventional surgical laparoscopic bipolar forceps for intra-abdominal vessel sealing in a porcine model", Gastrointestinal Endoscopy 2010, vol. 71, No. 4, pp. 835-841.
Fritscher-Ravens et al., "Beyond NOTES: randomized controlled study of different methods of flexible endoscopic hemostasis of artificially induced hemorrhage, via NOTES access to the peritoneal cavity", Endoscopy 2009, vol. 41, pp. 29-35.
Office Action dated Aug. 4, 2010 for U.S. Appl. No. 12/435,574, 7 pgs.
Response to Office Action filed Nov. 3, 2010 for U.S. Appl. No. 12/435,574, 13 pgs.
Office Action dated Feb. 17, 2011 for U.S. Appl. No. 12/435,574, 8 pgs.
Response to Office Action filed May 13, 2011 for U.S. Appl. No. 12/435,574, 15 pgs.
Office Action dated Aug. 22, 2011 for U.S. Appl. No. 12/435,574, 9 pgs.
Response to Office Action filed Nov. 22, 2011 for U.S. Appl. No. 12/435,574, 14 pgs.
Office Action dated Mar. 30, 2012 for U.S. Appl. No. 12/435,574, 9 pgs.
Response to Office Action filed Aug. 30, 2012 for U.S. Appl. No. 12/435,574, 18 pgs.
Office Action dated Oct. 2, 2014 for U.S. Appl. No. 12/435,574, 10 pgs.
Response to Office Action filed Feb. 24, 2015 for U.S. Appl. No. 12/435,574, 18 pgs.
Office Action dated Jun. 12, 2015 for U.S. Appl. No. 12/435,574, 10 pgs.
Response to Office Action filed Oct. 6, 2015 for U.S. Appl. No. 12/435,574, 19 pgs.
Office Action dated Jun. 1, 2016 for U.S. Appl. No. 12/435,574, 13 pgs.
Response to Office Action filed Aug. 2, 2016 for U.S. Appl. No. 12/435,574, 13 pgs.
Office Action dated Nov. 15, 2016 for U.S. Appl. No. 12/435,574, 15 pgs.
Notice of Allowance dated Aug. 10, 2017 for U.S. Appl. No. 12/435,574, 9 pgs.

* cited by examiner

APPARATUS AND METHODS FOR DELIVERING THERAPEUTIC AGENTS

PRIORITY CLAIM

The present patent document is a divisional application that claims the benefit of priority under 35 U.S.C. § 121 of U.S. patent application Ser. No. 12/435,574, filed May 5, 2009, which claims the benefit of priority of U.S. Provisional Application Ser. No. 61/050,906, filed May 6, 2008, both disclosures of which are hereby incorporated by reference in their entireties.

BACKGROUND

The present embodiments relate generally to medical devices, and more particularly, to apparatus and methods for delivering therapeutic agents to a target site.

There are several instances in which it may become desirable to introduce therapeutic agents into the human or animal body. For example, therapeutic drugs or bioactive materials may be introduced to achieve a biological effect. The biological effect may include an array of targeted results, such as inducing hemostasis, sealing perforations, reducing restenosis likelihood, or treating cancerous tumors or other diseases.

Many of such therapeutic agents are injected using an intravenous (IV) technique and via oral medicine. While such techniques permit the general introduction of medicine, in many instances it may be desirable to provide localized or targeted delivery of therapeutic agents, which may allow for the guided and precise delivery of agents to selected target sites. For example, localized delivery of therapeutic agents to a tumor may reduce the exposure of the therapeutic agents to normal, healthy tissues, which may reduce potentially harmful side effects.

Localized delivery of therapeutic agents has been performed using catheters and similar introducer devices. By way of example, a catheter may be advanced towards a target site within the patient, then the therapeutic agent may be injected through a lumen of the catheter to the target site. Typically, a syringe or similar device may be used to inject the therapeutic agent into the lumen of the catheter. However, such a delivery technique may result in a relatively weak stream of the injected therapeutic agent.

Moreover, it may be difficult or impossible to deliver therapeutic agents in a targeted manner in certain forms, such as a powder form, to a desired site. For example, if a therapeutic powder is held within a syringe or other container, it may not be easily delivered through a catheter to a target site in a localized manner that may also reduce potentially harmful side effects.

SUMMARY

The present embodiments provide apparatus and methods suitable for delivering a therapeutic agent to a target site. The apparatus generally comprises at least one container for holding a therapeutic agent, and a pressure source for facilitating delivery of the therapeutic agent.

In one embodiment, the pressure source may be placed in selective fluid communication with a proximal region of the container. Fluid from the pressure source may flow through at least a portion of the container to urge the therapeutic agent through a distal region of the container and towards the target site.

At least one tube member, such as a catheter, may be used to facilitate delivery of the therapeutic agent from the container to the target site. The tube member may be placed in fluid communication with the distal region of the container. In use, fluid from the pressure source urges the therapeutic agent through the distal region of the container, through the tube member, and then distally towards the target site.

The pressure source may comprise a compressed gas dispenser. Tubing may be disposed between the pressure source and the container, and optionally, a pressure relief valve may be disposed between the pressure source and the container. The pressure relief valve may ensure that the fluid from the pressure source flows through the container at a predetermined pressure.

In various other embodiments, a connecting member having first and second inlet ports and an outlet port is disclosed. The container and the pressure source may be coupled to the first and second inlet ports of the connecting member, respectively. In use, the provision of fluid from the pressure source through the second inlet port may suction the therapeutic agent from the container in a direction through the first inlet port. The fluid and the therapeutic agent then may flow through the outlet port of the connecting member and towards the target site. In this embodiment, at least one tube member may be coupled to the outlet port of the connecting member to facilitate delivery of the therapeutic agent from the connecting member to the target site.

In any of the embodiments disclosed, the distal region of the tube member may comprise an anti-reflux valve to inhibit flow of foreign substances, such as blood, proximally back into the system. The tube member also may be used in conjunction with a needle and may be configured to be delivered through a working lumen of an endoscope or similar device.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

In the present application, the term "proximal" refers to a direction that is generally towards a physician during a medical procedure, while the term "distal" refers to a direction that is generally towards a target site within a patient's anatomy during a medical procedure.

Figure 1:
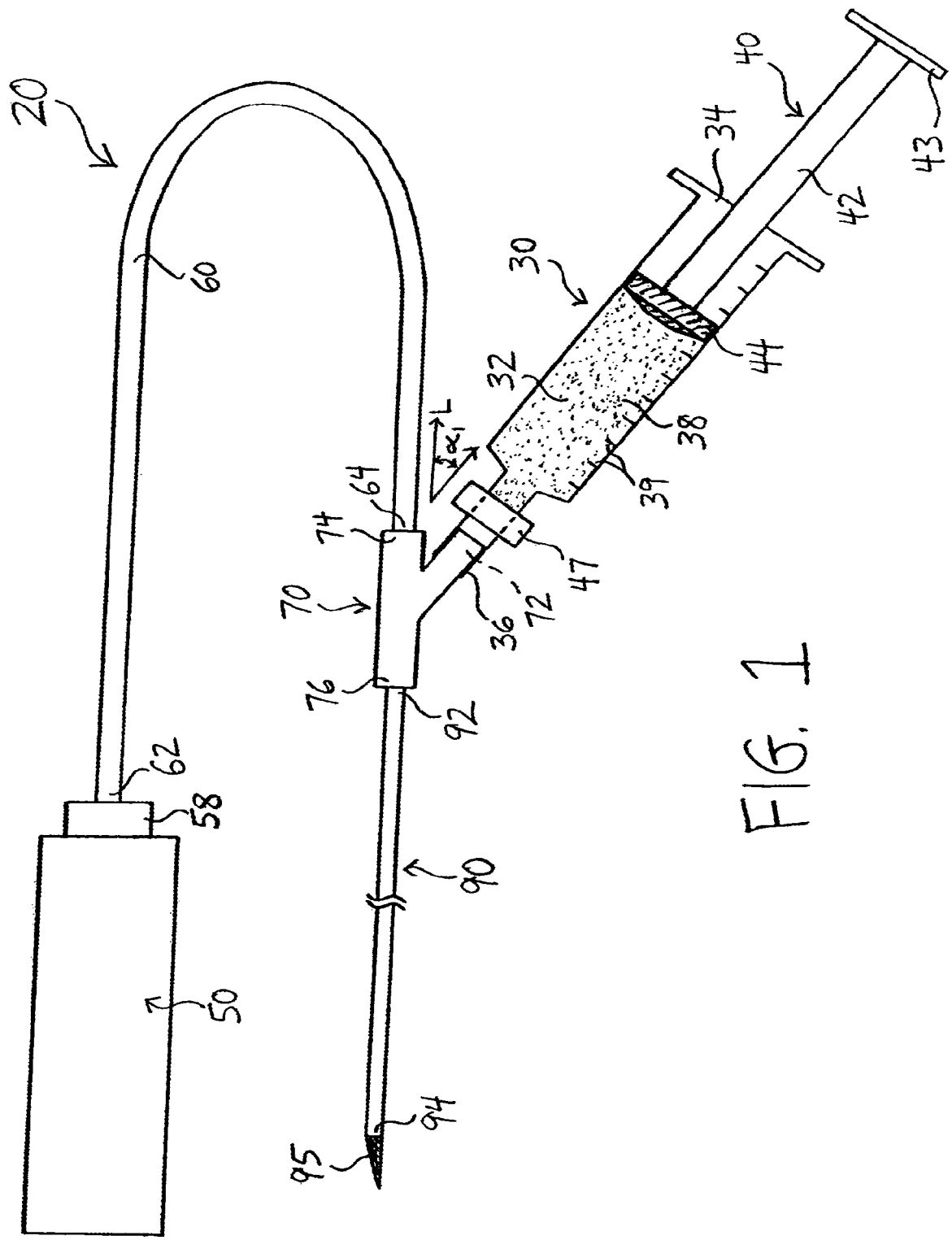
FIG. 1 is a schematic view of apparatus in accordance with a first embodiment.

Referring now to FIG. 1, a first embodiment of a system suitable for delivering one or more therapeutic agents is shown. In this embodiment, the system 20 comprises at least one container 30 that is configured to hold a therapeutic agent 38, and further comprises at least one pressure source 50. At least one connecting member 70 may be placed in fluid communication with the container 30 and the pressure source 50, as explained in further detail below.

The container 30 may comprise any suitable size and shape for holding a therapeutic agent 38. In one embodiment, the container 30 may comprise a syringe having a reservoir 32. A plunger 40 having a main body 42, a proximal handle 43, and a distal head member 44 may be disposed for longitudinal movement within the reservoir 32, preferably in a manner such that the distal head member 44 forms a substantial sealing engagement with an inner surface of the container 30.

The container 30 may comprise a hollow proximal region 34, through which the therapeutic agent 38 and the plunger 40 may be loaded, as shown in FIG. 1. The container 30 further may comprises a distal region 36 that is configured to be coupled to a first inlet port 72 associated with the connecting member 70, thereby enabling fluid communication between the container 30 and the connecting member 70.

The container 30 also may comprise measurement indicia 39, which allow a user to determine a quantity of the therapeutic agent 38 that is held within the container 30. Optionally, a valve member 47 may be disposed between the reservoir 32 of the container 30 and the connecting member 70, as shown in FIG. 1, to selectively permit and inhibit fluid communication between the container 30 and the connecting member 70, as described in greater detail below.

Figure 2:
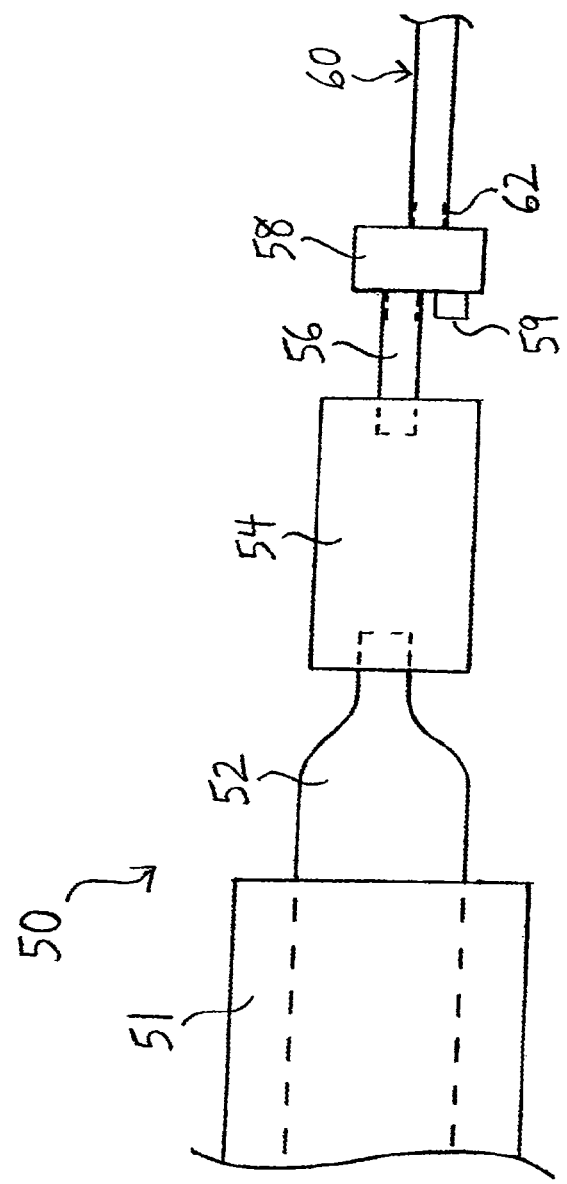
FIG. 2 is a side view illustrating selected components of an exemplary high pressure fluid source.

The pressure source 50 may comprise one or more components capable of producing or furnishing a fluid having a desired pressure. In one embodiment, the pressure source 50 may comprise a pressurized fluid, such as a liquid or gas. For example, as shown in FIG. 2, the pressure source 50 may comprise a housing 51 that covers a pressurized fluid cartridge 52 of a selected gas or liquid, such as carbon dioxide, nitrogen, or any other suitable gas or liquid that may be compatible with the human body. The pressurized fluid cartridge 52 may contain the gas or liquid at a relatively high, first predetermined pressure, for example, around 1,800 psi inside of the cartridge. The fluid may flow from the pressurized fluid cartridge 52 through a pressure regulator, such as regulator valve 58 having a pressure outlet 59, as depicted in FIGS. 1-2, which may reduce the pressure to a lower, second predetermined pressure. Solely by way of example, the second predetermined pressure may be in the range of about 30 to about 80 psi, although any suitable pressure may be provided for the purposes described below.

An actuator, such as a button, may be used to selectively actuate the pressure source 50. The pressurized fluid may flow from the pressurized fluid cartridge 52, and subsequently through the regulator valve 58 using an adapter 54. The adapter 54 may be configured to be sealingly coupled to the pressurized fluid cartridge 52, as shown in FIG. 2. Further, the adapter 54 may be coupled to tubing 56, which allows the pressurized fluid to flow into the regulator valve 58. A proximal end 62 of a different tubing 60 is adapted to be coupled to the regulator valve 58, as shown in FIG. 2, thereby enabling the pressurized fluid to flow through the regulator valve 58 and into the tubing 60 at the lower, second predetermined pressure.

The pressure source 50 optionally may comprise one or more commercially available components. Solely by way of example, the pressurized fluid cartridge 52 may comprise a disposable carbon dioxide cartridge, such as the Visage® commercial dispenser manufactured by Helen of Troy®, El Paso, Tex. The pressure source 50 therefore may comprise original or retrofitted components capable of providing a fluid or gas into the tubing 60 at a desired regulated pressure.

Referring still to FIG. 1, the connecting member 70 of the system 20 may comprise multiple ports configured to selectively permit and inhibit fluid communication between the various components. In one embodiment, the connecting member 70 comprises first and second inlet ports 72 and 74 and an outlet port 76. As noted above, the distal region 36 of the container 30 may be coupled to the first inlet port 72 of the connecting member 70, thereby enabling selective fluid communication between the container 30 and the connecting member 70, as depicted in FIG. 1. Any suitable coupling mechanism may be employed, for example, the distal region 36 of the container 30 may be configured to form a frictional fit with the first inlet port 72, or may comprise a threaded engagement or similar coupling arrangement. Similarly, a distal end 64 of the tubing 60 may be coupled to the second inlet port 74 of the connecting member 70 using any suitable coupling mechanism or arrangement.

In the embodiment of FIG. 1, the second inlet port 74 and the outlet port 76 are generally aligned with a longitudinal axis L of the connecting member 70, while the first inlet port 72 is disposed at an angle $\alpha_1$ with respect to the longitudinal axis L. However, as will be described further below, the connecting member may employ different shapes such that various components may be disposed at different angles with respect to the connecting member.

The system 20 further may comprise one or more tube members for delivering the therapeutic agent 38 to a target site. For example, the tube member may comprise a catheter 90 having a proximal end 92 that may be placed in fluid communication with the outlet port 76 of the connecting member 70 using a suitable coupling mechanism or arrangement. The catheter 90 further comprises a distal end 94 that may facilitate delivery of the therapeutic agent 38 to a target site, as set forth below. The catheter 90 may comprise a flexible, tubular member that may be formed from one or more semi-rigid polymers. For example, the catheter may be manufactured from polyurethane, polyethylene, tetrafluoroethylene, polytetrafluoroethylene, fluorinated ethylene propylene, nylon, PEBAX or the like.

The system 20 further may comprise a needle 95 suitable for penetrating tissue. As shown in the embodiment of FIG. 1, the needle 95 may be coupled to the distal end 94 of the catheter 90 to form a sharp, distal region configured to pierce through a portion of a patient's tissue, or through a lumen wall to perform a translumenal procedure. In FIG. 1, the needle 95 may be formed as an integral component with the catheter 90, i.e., such that distal movement of the catheter 90 causes distal advancement of the needle 95. In this embodiment, a relatively sharp needle tip may be affixed to the distal tip of the catheter 90, e.g., using an adhesive, to form a needle-shaped element at the distal end of the catheter. Alternatively, a separate needle configured to be inserted through a lumen of the catheter 90 may be employed.

In operation, the system of FIG. 1 may be used to deliver the therapeutic agent 38 to a target site within a patient's body. In a first step, the distal end 94 of the catheter 90 may be positioned in relatively close proximity to the target site. The catheter 90 may be advanced to the target site using an open technique, a laparoscopic technique, an intraluminal technique, using a gastroenterology technique through the mouth, colon, or using any other suitable technique.

The catheter 90 may comprise one or more markers (not shown), which may be disposed near the distal end of the catheter 90. The markers may be configured to be visualized under fluoroscopy or other imaging techniques to facilitate location of the distal end 94 of the catheter 90. If the needle 95 is integral to the catheter 90, the needle 95 also may be visualized using the imaging techniques, thereby allowing placement of the distal end 94 of the catheter 90 in close proximity to the target site. If desired, the catheter 90 may be advances through a working lumen of an endoscope, as explained in further detail in FIGS. 3-4 below.

When the catheter 90 is positioned at the desired location, the pressure source 50 may be actuated. For example, a suitable actuator may be coupled to the pressurized fluid cartridge 52 to release a relatively high pressure fluid. As noted above, the pressurized fluid may flow through a regulator valve 58 and through the tubing 60, as depicted in FIG. 1. Fluid injected through the tubing 60 may flow at a desired pressure and rate. For example, the regulator valve 58 may automatically set the pressure for fluid flow, or alternatively, a control mechanism coupled to the pressurized fluid cartridge 52 and/or the regulator valve 58 may be activated by a user to set the desired pressure for fluid flow into the tubing 60. Such a control mechanism also may be used to variably permit fluid flow into the tubing 60, e.g., fluid from the pressurized fluid cartridge 52 may flow into the tubing 60 at a desired time interval, for example, a predetermined quantity of fluid per second. Moreover, the control mechanism may be pre-programmed to deliver a predetermined amount of the therapeutic agent, depending on the type, viscosity, and other properties of the agent. Empirical information, such as a table of pressure, time and delivered quantity, may be stored and used for the different agents or procedures.

Fluid from the pressure source 50 flows through the tubing 60, through the second inlet port 74 of the connecting member 70, and then through the outlet port 76 of the connecting member 70 and through a lumen of the catheter 90. Fluid may exit the distal end 94 of the catheter 90, for example, through a bore formed in the needle 95.

As fluid from the pressure source 50 passes through the connecting member 70, a localized low pressure system will be provided in the vicinity of the second inlet port 72 in accordance with Bernoulli's principle of fluid dynamics. The low pressure system formed by the presence of the pressurized fluid passing through the connecting member 70 will form a strong suction force when it passes by the second inlet port 72. As a result, the therapeutic agent 38 may be suctioned out of the reservoir 32 of the container 30 and through the second inlet port 72. Moreover, the therapeutic agent 38 may be carried through the outlet port 76 of the connecting member 70 by the pressurized fluid, and subsequently through the catheter 90, thereby delivering the therapeutic agent 38 to the target site at a desired pressure.

The therapeutic agent 38 may be drawn out of the reservoir 32 by the mere presence of the pressurized fluid flow through the connecting member 70, i.e., with minimal or no user intervention. In this embodiment, the user simply may load the desired therapeutic agent 38 into the reservoir 32, then load the plunger 40 into the proximal region 34 of the container 30. The provision of the pressurized fluid flow through the connecting member 70 may suction the therapeutic agent 38 from the reservoir 32 and may urge the plunger 40 in a distal direction until the contents of the container 30 are dispensed.

In addition to the automatic withdrawal of the therapeutic agent 38 from the container 30 in accordance with Bernoulli's principle, a user may manually actuate the proximal handle 43 of the plunger 40 to dispense the therapeutic agent 38. For example, in this instance, after a user has loaded a desired amount of the therapeutic agent 38 into the reservoir 32, the user may manually actuate the proximal handle 43 of the plunger 40 to dispense the therapeutic agent 38 from the container 30 and at least partially into interior regions of the connecting member 70 and/or the catheter 90. The plunger 40 may be manually actuated in this manner before, during or after the pressure source 50 has been actuated to deliver pressurized fluid through the connecting member 70 and the catheter 90.

As noted above, a valve member 47 optionally may be disposed between the reservoir 32 of the container 30 and the connecting member 70, as shown in FIG. 1. A user may selectively actuate the valve member 47 to periodically permit and inhibit fluid communication between the container 30 and the connecting member 70. The valve member 47 also may serve as a "shut-off" safety mechanism to inhibit withdrawal of the therapeutic agent 38 from the reservoir 32, even when pressurized fluid is flowing through the connecting member 70.

As noted above, a control mechanism coupled to the pressure source 50 may variably permit fluid flow into the tubing 60 from the pressurized fluid cartridge 52 at a desired time interval, for example, a predetermined quantity of fluid per second. In this manner, pressurized fluid may flow through the connecting member 70 periodically, and the therapeutic agent 38 may be suctioned from the reservoir 32 and delivered to a target site at a predetermined interval or otherwise periodic basis.

The system 20 may be used to delivery the therapeutic agent 38 in a wide range of procedures and the therapeutic agent 38 may be chosen to perform a desired function upon ejection from the distal end 94 of the catheter 90. Solely by way of example, and without limitation, the provision of the therapeutic agent 38 may be used for providing hemostasis, closing perforations, performing lithotripsy, treating tumors and cancers, treat renal dialysis fistulae stenosis, vascular graft stenosis, and the like. The therapeutic agent 38 can be delivered during procedures such as coronary artery angioplasty, renal artery angioplasty and carotid artery surgery, or may be used generally for treating various other cardiovascular, respiratory, gastroenterology or other conditions. The above-mentioned systems also may be used in transvaginal, umbilical, nasal, and bronchial/lung related applications.

For example, if used for purposes of hemostasis, thrombin, epinephrine, or a sclerosant may be provided to reduce localized bleeding. Similarly, if used for closing a perforation, a fibrin sealant may be delivered to a localized lesion. In addition to the hemostatic properties of the therapeutic agent 38, it should be noted that the relatively high pressure of the fluid and therapeutic agent, by itself, may act as a mechanical tamponade by providing a compressive force, thereby reducing the time needed to achieve hemostasis.

The therapeutic agent 38 may be selected to perform one or more desired biological functions, for example, promoting the ingrowth of tissue from the interior wall of a body vessel, or alternatively, to mitigate or prevent undesired conditions in the vessel wall, such as restenosis. Many other types of therapeutic agents 38 may be used in conjunction with the system 20.

The therapeutic agent 38 may be delivered in any suitable form. For example, the therapeutic agent 38 may comprise a powder, liquid, gel, aerosol, or other substance. Advantageously, the pressure source 50 may facilitate delivery of the therapeutic agent 38 in any one of these forms.

The therapeutic agent 38 employed also may comprise an antithrombogenic bioactive agent, e.g., any bioactive agent that inhibits or prevents thrombus formation within a body vessel. Types of antithrombotic bioactive agents include anticoagulants, antiplatelets, and fibrinolytics. Anticoagulants are bioactive materials which act on any of the factors, cofactors, activated factors, or activated cofactors in the biochemical cascade and inhibit the synthesis of fibrin. Antiplatelet bioactive agents inhibit the adhesion, activation, and aggregation of platelets, which are key components of thrombi and play an important role in thrombosis. Fibrinolytic bioactive agents enhance the fibrinolytic cascade or otherwise aid in dissolution of a thrombus. Examples of antithrombotics include but are not limited to anticoagulants such as thrombin, Factor Xa, Factor VIIa and tissue factor inhibitors; antiplatelets such as glycoprotein IIb/IIIa, thromboxane A2, ADP-induced glycoprotein IIb/IIIa, and phosphodiesterase inhibitors; and fibrinolytics such as plasminogen activators, thrombin activatable fibrinolysis inhibitor (TAFI) inhibitors, and other enzymes which cleave fibrin.

Additionally, or alternatively, the therapeutic agent 38 may include thrombolytic agents used to dissolve blood clots that may adversely affect blood flow in body vessels. A thrombolytic agent is any therapeutic agent that either digests fibrin fibers directly or activates the natural mechanisms for doing so. Examples of commercial thrombolytics, with the corresponding active agent in parenthesis, include, but are not limited to, Abbokinase (urokinase), Abbokinase Open-Cath (urokinase), Activase (alteplase, recombinant), Eminase (anitstreplase), Retavase (reteplase, recombinant), and Streptase (streptokinase). Other commonly used names are anisoylated plasminogen-streptokinase activator complex; APSAC; tissue-type plasminogen activator (recombinant); t-PA; rt-PA. While a few exemplary therapeutic agents 38 have been listed, it will be apparent that numerous other suitable therapeutic agents may be used in conjunction with the system 20 and delivered through the catheter 90.

Advantageously, the system 20 permits localized delivery of a desired quantity of the therapeutic agent 38 at a desired pressure via the pressure source 50. Since the distal end 94 of the catheter 90 may be placed in relatively close proximity to a target site, the system 20 provides significant advantages over therapeutic agents delivered orally or through an IV system and may reduce accumulation of the therapeutic agent 38 in healthy tissues, thereby reducing side effects. Moreover, the delivery of the therapeutic agent 38 to the target site is performed in a relatively fast manner due to the relatively high pressure of the fluid, thereby providing a prompt delivery to the target site compared to previous devices.

Further, if the optional needle 95 is employed, the system 20 advantageously may be used to both perforate tissue at or near a target site, then deliver the therapeutic agent 38 at a desired pressure in the manner described above. For example, the needle 95 may comprise an endoscopic ultrasound (EUS) needle. Accordingly, in one exemplary technique, a sharpened tip of the needle 95 may be capable of puncturing through an organ or a gastrointestinal wall or tissue, so that the therapeutic agent 38 may be delivered at a predetermined pressure in various bodily locations that may be otherwise difficult to access. One or more delivery vehicles, such as an endoscope or sheath, may be employed to deliver the catheter 90 to a target site, particularly if the distal end 94 of the catheter 90 comprises the optional needle 95.

Figure 3:
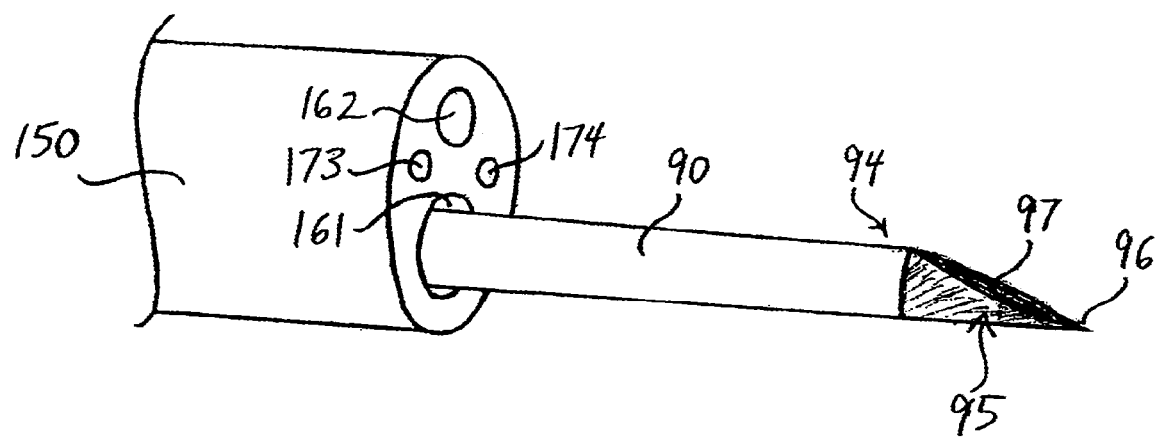
FIG. 3 is a perspective view of the distal end of an exemplary end-viewing endoscope that may be used in conjunction with the system of FIG. 1.
Figure 4:
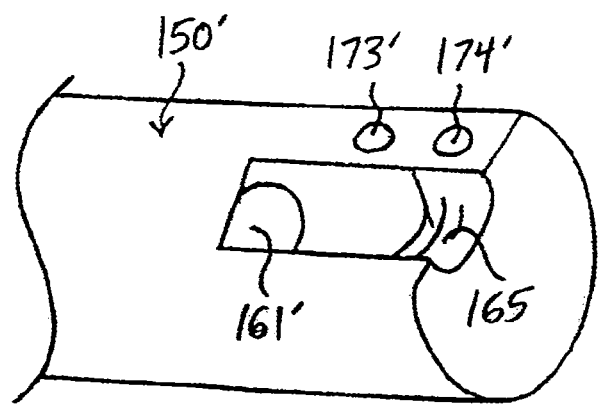
FIG. 4 is a perspective view of the distal end of an exemplary side-viewing endoscope that may be used in conjunction with the system of FIG. 1.

Referring now to FIGS. 3-4, exemplary endoscopes that may be used in conjunction with the system 20 are described. In FIG. 3, an end-viewing endoscope 150 comprises optical elements 173 and 174 disposed on the distal end surface of the endoscope, which employ fiber optic components for illuminating and capturing an image distal to the endoscope. Further, a working channel 161 extends through the distal end surface of the endoscope 150, as shown in FIG. 3. The working channel 161 may be sized to accommodate the catheter 90 therein for purposes of longitudinally advancing the catheter 90 to the target site. As shown, one auxiliary lumen 162 also optionally may be provided, although greater or fewer lumens/channels may be employed.

The endoscope 150 may be advanced through a bodily lumen such as the alimentary canal to a position proximate the target location. The catheter 90 then may be advanced through the working lumen 161 of the endoscope 150. If the needle 95 is employed, a sharpened tip 96 of the needle 95 may extend distal to the endoscope 150, as shown in FIG. 3, and may be used to puncture through an organ or a gastrointestinal wall or tissue. At this time, the therapeutic agent 38 may be delivered through the catheter 90, then through a bore 97 in the needle 95, in the manner described above.

In FIG. 4, a side-viewing endoscope 150' is similar to the end-viewing endoscope 150, with the main exception that optical elements 173' and 174' are disposed on a side surface of the endoscope 150' and capable of capturing an image to the side of the endoscope. The endoscope 150' preferably comprises a working channel 161', which is sized to accommodate the catheter 90 therein for purposes of longitudinally advancing the catheter to a target site. A guiding channel 165 may be formed near the distal surface of the endoscope 150' to cause components advanced through the working channel 161' to exit at a predetermined angle with respect to a longitudinal axis of the endoscope 150'. It will be apparent that while one working channel 161' is shown, the endoscope 150' may comprise at least one more additional lumen or channel, such as an auxiliary lumen.

Figure 5:
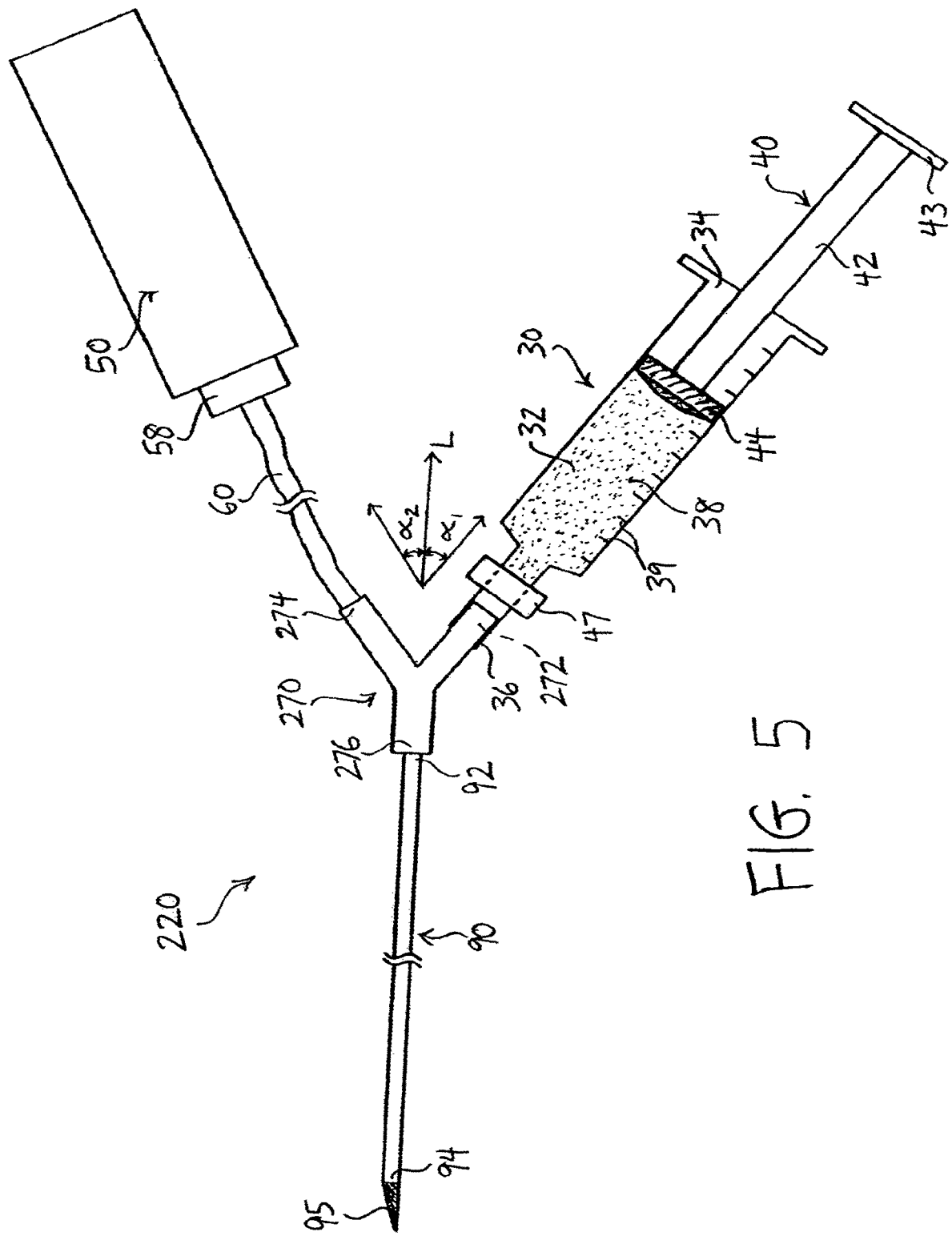
FIG. 5 is a schematic view of apparatus in accordance with an alternative embodiment.

Referring now to FIG. 5, an alternative system 220 for delivery therapeutic agents is similar to system 20 of FIG. 1, both in structure and general operation, with main exceptions noted below. In FIG. 5, the alternative system 220 comprises a generally Y-shaped connecting member 270, which has a slightly different shape relative to the connecting member 70 of FIG. 1. Specifically, the connecting member 270 has first and second inlet ports 272 and 274, respectively, and an outlet port 276. The outlet port 276 may be aligned with a longitudinal axis L, as shown in FIG. 5. The first inlet port 272 may be disposed at an angle $\alpha_1$ with respect to the axis of the outlet port 276, while the second inlet port 274 may be disposed at an angle $\alpha_2$ with respect to the outlet port 276, as depicted in FIG. 5. The angles $\alpha_1$ and $\alpha_2$ are depicted as being substantially identical in FIG. 5, at about 25-45 degrees, which may facilitate mixing and/or flow of the contents through the connecting member 270 and out of the outlet port 276. However, it will be apparent that any suitable angle may be employed and that the angles $\alpha_1$ and $\alpha_2$ may comprise different angles.

Figure 6:
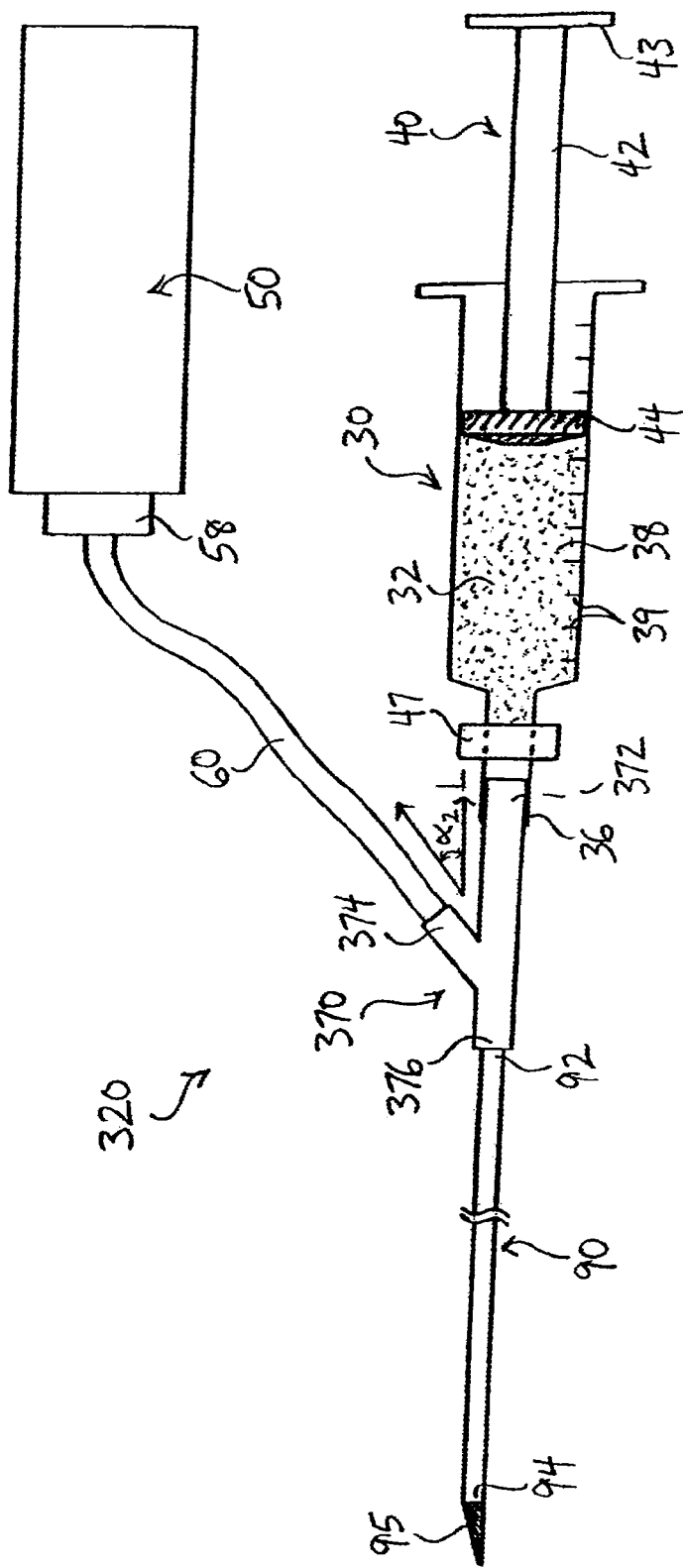
FIG. 6 is a schematic view of apparatus in accordance with a further alternative embodiment.

Referring now to FIG. 6, an alternative system 320 for delivery therapeutic agents is shown. The alternative system 320 is similar to system 20 of FIG. 1, both in structure and general operation, with a main exception that alternative connecting member 370 has a first inlet port 372 aligned with the longitudinal axis L, and a second inlet port 374 disposed at an angle $\alpha_2$ with respect to the outlet port 376. Further, in this embodiment, the second inlet port 374 is placed in closer proximity to the outlet port 376, in relation to the positioning of the first inlet port 372, as shown in FIG. 6. In this embodiment, like the others described above, the fluid from the pressure source 50 passes through the second inlet port 374 and into the alternative connecting member 370 to create a localized low pressure system in the vicinity of the first inlet port 372. The low pressure system will form a strong suction force to suction the therapeutic agent 38 out of the reservoir 32, through the first inlet port 372 and through the catheter 90.

Figure 7:
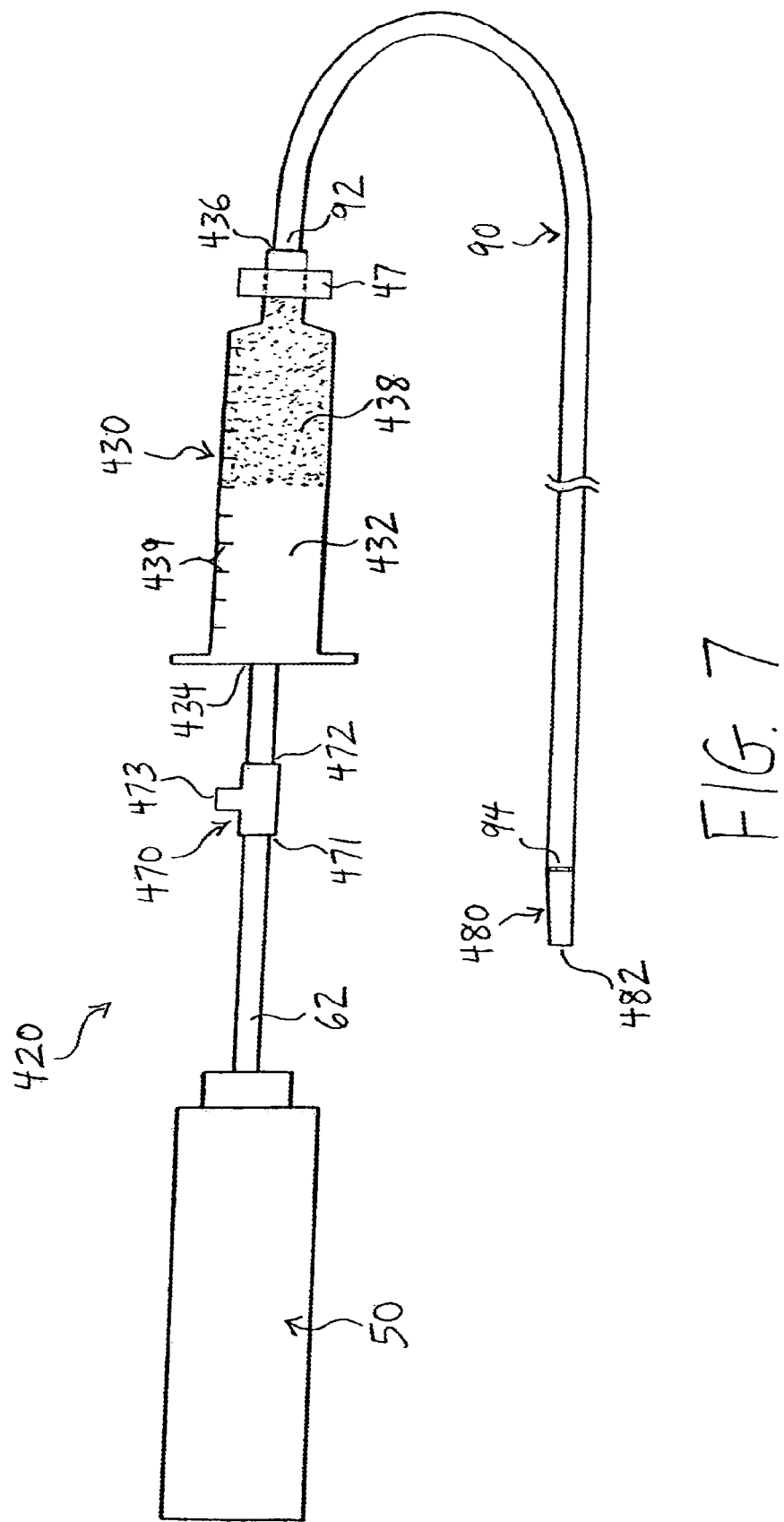
FIG. 7 is a schematic view of apparatus in accordance with yet a further alternative embodiment.

Referring now to FIG. 7, an alternative system 420 for delivery therapeutic agents is described. The alternative system 420 is similar to system 20 of FIG. 1 in general operation, with main exceptions noted below. Notably, in the embodiment of FIG. 7, fluid from the pressure source 50 may be passed directly through a proximal region 434 of the container 430. In this embodiment, the plunger of the container may be omitted. A therapeutic agent 438 is provided within a reservoir 432 using measurement indicia 439. Tubing 62 may be coupled between the pressure source 50 and the proximal region 434 of the container 430. When the pressure source 50 is actuated, a high pressure fluid may flow directly through the container 430 to urge the therapeutic agent 438 out of a distal region 436 of the container 430 and into the catheter 90.

Additionally, in the embodiment of FIG. 7, a pressure relief valve 470 may be disposed between the pressure source 50 and the container 430. The pressure relief valve 470 may be similar to the regulator valve 58 of FIG. 1, and may comprise first and second ports 471 and 472 having an outlet valve 473 disposed therebetween. In operation, if fluid from the pressure source 50 exceeds a predetermined pressure, the pressure relief valve 470 may reduce the pressure that flows out of the second port 472 and into the container 430.

Finally, the alternative system 420 further comprises an anti-reflux valve 480 coupled to the distal end 94 of the catheter 90, as shown in FIG. 7. In use, the anti-reflux valve 480 may be configured to prevent blood or other foreign fluids from entering a distal opening 482 of the valve, and then flowing proximally into the catheter 90, which may lead to complications such as occlusion in the system 420. While the anti-reflux valve 480 is shown in use in the embodiment of FIG. 7, it will be apparent that it may be used in lieu of the needle 95 in conjunction with the embodiments of FIGS. 1, 5 and 6. Conversely, the needle 95 of the above-mentioned embodiments may be coupled to the distal end 94 of the catheter 90 in the embodiment of FIG. 7.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

I claim:

1. A method suitable for delivering at least one therapeutic agent to a target site, the method comprising:
   providing at least one container having proximal and distal regions, wherein the container holds a therapeutic agent;
   placing a pressure source in selective fluid communication with the proximal region of the container;
   actuating the pressure source to cause fluid to flow through at least a portion of the container to both a) generate a mixture of fluid from the pressure source and the therapeutic agent and b) urge the mixture of the fluid from the pressure source and the therapeutic agent concurrently through the distal region of the container and then through a tube member in a distal direction towards the target site; and
   selectively inhibiting flow of the mixture of the fluid from the pressure source and the therapeutic agent using a valve having a proximal end and a distal end, wherein the proximal end and the distal end of the valve are disposed distal to the container and proximal to the tube member.

2. The method of claim 1, wherein the therapeutic agent comprises a powder.

3. The method of claim 1, wherein the pressure source comprises a compressed gas dispenser.

4. The method of claim 1, further comprising placing a tube between the pressure source and the container.

5. The method of claim 1, further comprising placing a pressure relief valve between the pressure source and the container.

6. A method suitable for delivering at least one therapeutic agent to a target site, the method comprising:
   positioning a distal end of a tube member adjacent to a target site, wherein a proximal end of the tube member is coupled to a distal region of a container holding a therapeutic agent;
   actuating a pressure source to cause fluid to flow through a proximal region of the container to both a) generate a mixture of the fluid from the pressure source and the therapeutic agent and b) urge the mixture of the fluid from the pressure source and the therapeutic agent to flow concurrently through the distal region of the container and then through the tube member in a distal direction towards the target site; and
   selectively inhibiting flow of the mixture of the fluid from the pressure source and the therapeutic agent using a valve having a proximal end and a distal end, wherein the proximal end and the distal end of the valve are disposed distal to the container and proximal to the tube member.

7. The method of claim 6, wherein the therapeutic agent comprises a powder.

8. The method of claim 6, wherein the pressure source comprises a compressed gas dispenser.

9. The method of claim 6 further comprising:
   providing tubing disposed between the pressure source and the container; and
   providing a pressure relief valve disposed between the pressure source and the container.

10. A method suitable for delivering at least one therapeutic agent to a target site, the method comprising:
    placing a pressure source in selective fluid communication with a proximal region of a container, wherein the container holds a therapeutic agent;

positioning a distal end of a tube member adjacent to a target site, wherein a proximal end of the tube member is coupled to a distal region of the container;

actuating the pressure source to cause fluid to flow through at least a portion of the container to both a) generate a mixture of fluid from the pressure source and the therapeutic agent and b) urge the mixture from the pressure source and the therapeutic agent concurrently through the distal region of the container and then through the tube member in a distal direction towards the target site;

wherein the therapeutic agent comprises a powder; and wherein the pressure source comprises a compressed gas dispenser.

11. The method of claim 10, further comprising selectively inhibiting flow of the mixture of the fluid from the pressure source and the therapeutic agent using a valve disposed proximal to the tube member.

12. The method of claim 10, further comprising placing a tube between the pressure source and the container.

13. The method of claim 10, further comprising placing a pressure relief valve between the pressure source and the container.

* * * * *